United States Patent [19]
Eger

[11] Patent Number: 5,812,239
[45] Date of Patent: Sep. 22, 1998

[54] METHOD OF AND ARRANGEMENT FOR THE ENHANCEMENT OF VISION AND/OR HAND-EYE COORDINATION

[76] Inventor: Jeffrey J. Eger, 7520 S. Forrest Ave., Tempe, Ariz. 85283

[21] Appl. No.: 735,006

[22] Filed: Oct. 22, 1996

[51] Int. Cl.[6] .................................. A61B 3/00; A61B 3/02
[52] U.S. Cl. .......................... 351/203; 351/224; 351/243
[58] Field of Search ................................... 351/203, 224, 351/226, 243

[56] References Cited

U.S. PATENT DOCUMENTS

| | | | |
|---|---|---|---|
| 3,737,217 | 6/1973 | Haines et al. | 351/224 |
| 4,824,237 | 4/1989 | Ratner et al. | 351/203 |
| 4,940,323 | 7/1990 | Dowing | 351/203 |

*Primary Examiner*—Huy Mai
*Attorney, Agent, or Firm*—Antonio R. Durando

[57] ABSTRACT

An arrangement for enhancing vision and/or hand-eye coordination includes a foldable or bendable sheet. The sheet carries a circular array of annular pads, and a light-emitting diode fits in the center of each pad. The pads and light-emitting diodes can be connected to a microprocessor which, in turn, can be connected to a display unit. The microprocessor can be programmed to illuminate the light-emitting diodes in different sequences. The sheet is suspended and a subject stands in front of the sheet. As different light-emitting diodes are illuminated, the subject attempts to follow the motion with her/his eyes. Alternatively, the subject attempts to extinguish an illuminated light-emitting diode by touching, or propelling an object against, the associated pad. The microprocessor can establish a score or rating for the subject, and the results can be shown on the display unit. In exercise or training regimes where the subject must focus on an object, the sheet can be provided with a central opening which permits the subject to look through the sheet and focus at virtual infinity. The opening can also accept a unit which instead allows the subject to focus at optical infinity. In exercise or training regimes where the subject propels an object towards the sheet, the sheet may be provided with small microphones which can record the location and strength of impacts.

32 Claims, 5 Drawing Sheets

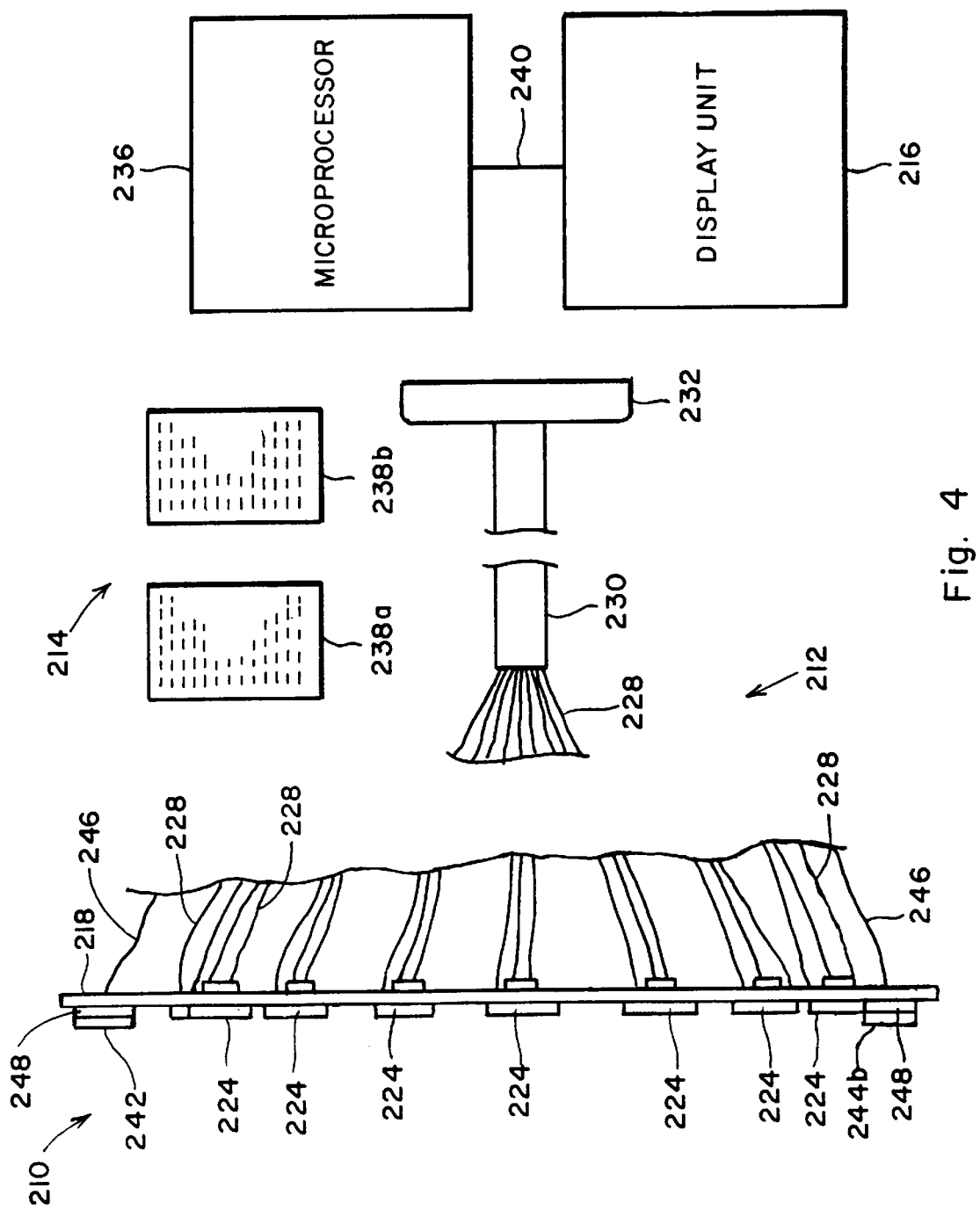

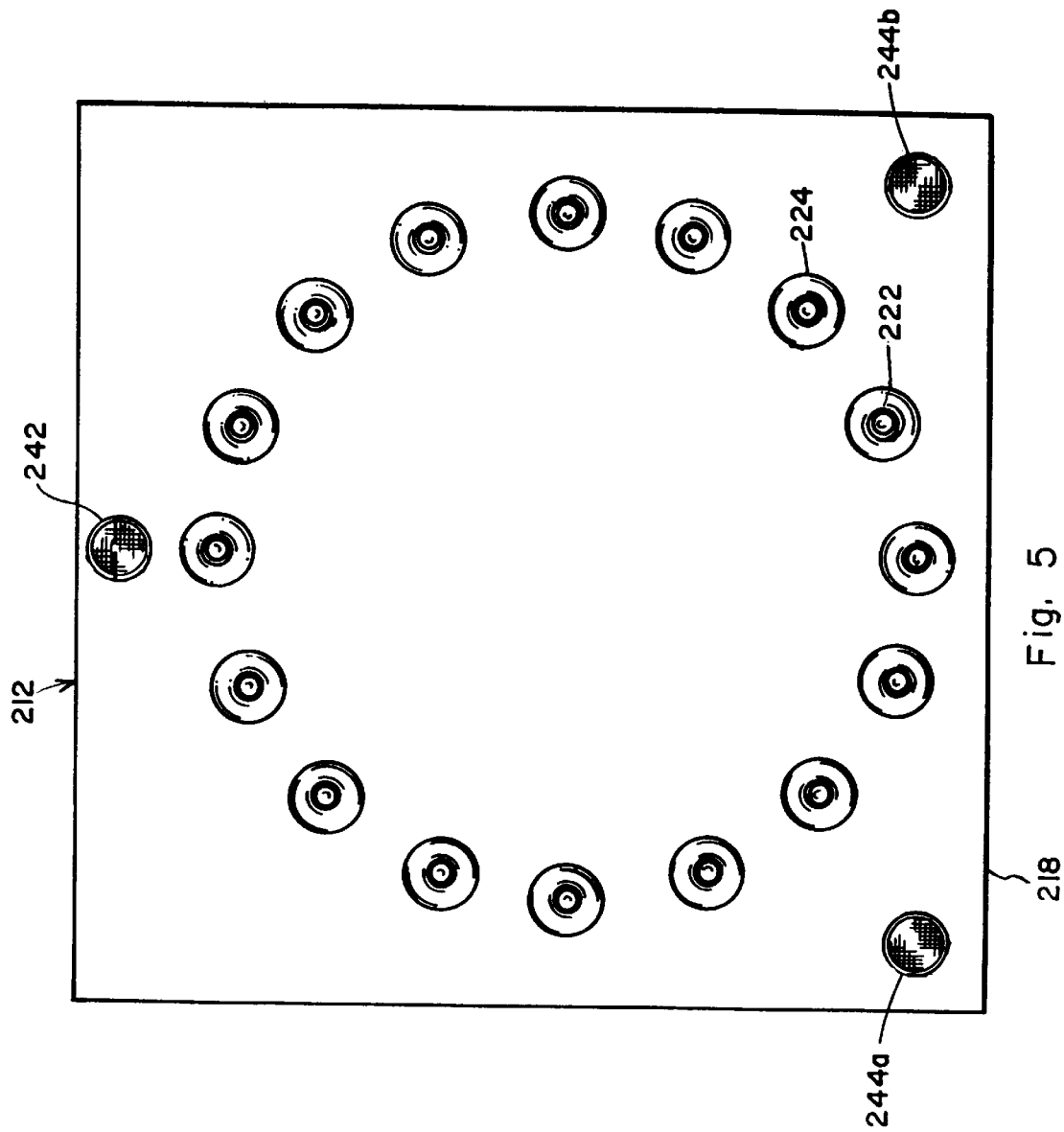

METHOD OF AND ARRANGEMENT FOR THE ENHANCEMENT OF VISION AND/OR HAND-EYE COORDINATION

BACKGROUND OF THE INVENTION

1. Field of the Invention

The invention relates to the enhancement of vision and/or hand-eye coordination.

2. Description of the Prior Art

Good peripheral vision and hand-eye coordination are important in a variety of situations. For example, certain athletic activities require both a heightened ability to see peripherally and superior hand-eye coordination. As a result, equipment for enhancing peripheral vision and hand-eye coordination has been developed.

Equipment of this type is disclosed in U.S. Pat. No. 4,824,237. The equipment includes a housing which slidably receives a molded screen defining a grid of lamp positions and dummy positions. An electronic component board is slidably mounted behind the screen and is provided with light emitting diodes and contacts at the lamp positions. The screen has openings at the lamp positions and a pushbutton is mounted in each of the openings. The pushbuttons carry contacts, and pulses are generated when the pushbuttons are depressed so that the contacts on the pushbuttons touch the contacts on the electronic component board. The screen has simulated pushbuttons at the dummy positions in order to make the latter virtually indistinguishable from the lamp positions.

In one mode of operation, the lamps are illuminated sequentially in a continuous moving pattern. A subject stands in front of the screen and follows the movement with her/his eyes. In another mode of operation, the lamps are illuminated in a random sequence and the subject attempts to depress a pushbutton while the corresponding lamp is illuminated. A control unit keeps count of the number of pushbuttons which were activated in a timely manner. For this mode of operation, the electronic component board may be provided with a centrally located, blue fixator light which is turned on and off at a predetermined rate. The subject keeps her/his eyes focused on the fixator light while reaching for the pushbuttons.

Another embodiment of the equipment disclosed in U.S. Pat. No. 4,824,237 includes a rod with a linear array of lamps. One end of the rod carries a shock absorber having a clamp which can be affixed to a vertical track. The clamp permits the rod to be positioned at different heights. The lamp at the end of the rod remote from the shock absorber is encased in a clear silicone bumper provided with a switch. In operation, the lamps are illuminated sequentially from the shock absorber to the bumper. A subject attempts to strike the bumper, e.g., with a bat, tennis racket or foot, while the lamp in the bumper is illuminated. A control unit indicates whether the bumper was struck early, late or on time. This mode of operation allows the subject to simulate striking of a moving object such as a baseball, tennis ball or soccer ball.

Since, from the point of view of a subject, the fixator lamp in the equipment of U.S. Pat. No. 4,824,237 appears to be relatively close, the subject is not entirely relaxed when focusing on the lamp and does not benefit fully from the exercise being performed. Furthermore, the equipment is relatively bulky and therefore not easy to transport from one location to another. Moreover, the pushbutton design requires substantial pressure in order to generate a pulse. In addition, while the embodiment with the rod provides data on timing, it is unable to supply information on accuracy.

SUMMARY OF THE INVENTION

It is an object of the invention to provide equipment which enables a subject to focus in a more relaxed manner.

Another object of the invention is to provide equipment which can be transported relatively easily.

An additional object of the invention is to provide equipment which makes it possible to produce data on both timing and accuracy.

A further object of the invention is to provide equipment which allows pulses to be generated with relatively little pressure.

One more object of the invention is to provide a method which permits more relaxed focusing to be achieved.

It is also an object of the invention to provide a method which enables equipment used for the method to be transported with relative ease.

Yet another object of the invention is to provide a method which makes it possible to generate data on timing as well as accuracy.

An additional object of the invention is to provide a method which allows pulses to be produced with relatively little pressure.

The preceding objects, as well as others which will become apparent as the description proceeds, are achieved by the invention.

One aspect of the invention resides in an arrangement for enhancing vision and/or hand-eye coordination.

In one embodiment, the arrangement comprises a plurality of light sources, a control system for controlling illumination of the light sources, and means for permitting the eyes to fixate at virtual or optical infinity while maintaining the light sources within peripheral vision range.

Fixation at virtual or optical infinity is more relaxing than fixation at a location which appears to be close. Inasmuch as a subject derives greater benefit from an exercise when the subject relaxes, the invention allows the effects of exercise to be enhanced.

Another embodiment of the arrangement comprises a plurality of light sources, a control system for controlling illumination of the light sources, and a foldable or roll-up carrier for the light sources.

The foldable or roll-up character of the carrier allows the carrier to be made more compact thereby facilitating transport of the carrier.

An additional embodiment of the arrangement comprises a plurality of light sources, an audio element, a carrier for the light sources and the audio element, and a control system for controlling illumination of the light sources and recording data generated by the audio element in response to impacts on the carrier.

The audio element is designed to pick up the sound of an impact on the carrier. The signal from the audio element can then be used to determine not only the timing of the impact but also the location of the impact.

A further embodiment of the arrangement comprises a plurality of light sources, a control system for controlling illumination of the light sources, and an extinguishing element for at least one of the light sources. The extinguishing element is designed to at least partially circumscribe the respective light source and to extinguish the latter in response to touch.

Since the extinguishing element is responsive to touch, little pressure is required for activation so that the extinguishing element is easy to operate.

Another aspect of the invention resides in a method of enhancing vision and/or hand-eye coordination.

One embodiment of the method comprises the steps of fixating at virtual or optical infinity, illuminating light sources within peripheral vision range during the fixating step, and reacting to illumination of the light sources.

The light sources may be illuminated sequentially. The reacting step may include reaching for a light source upon illumination of the same. The reacting step may also include extinguishing an illuminated light source by touch.

The illuminating and reacting steps can be performed in a darkened atmosphere and the fixating step then involves observing an illuminated object. The method may here additionally comprise the step of filtering illumination from the object. The light sources can be green and, under such circumstances, the illumination from the object is colored red by filtering. It is further possible for the light sources to be red in which case the illumination from the object is filtered so as to be colored blue.

Another embodiment of the method comprises the steps of distributing light sources within peripheral vision range, illuminating the light sources, reacting to illumination of the light sources, and gathering the light sources subsequent to the illuminating and reacting steps.

The light sources may be mounted on a carrier and the gathering step then involves folding or rolling up the carrier.

An additional embodiment of the method comprises the steps of illuminating light sources within peripheral vision range, reacting to illumination of a predetermined light source by impacting an area around the predetermined light source, and recording the sound of the impact.

In this embodiment, the method may further comprise the step of displaying data relating to the recording step.

A further embodiment of the method comprises the steps of illuminating light sources within peripheral vision range, and reacting to illumination of a predetermined light source, including extinguishing the predetermined light source by touch.

Each embodiment of the method can additionally comprise the steps of recording and displaying data relating to the reacting step.

Other features and advantages of the invention will be forthcoming from the following detailed description of preferred embodiments when read in conjunction with the accompanying drawings.

BRIEF DESCRIPTION OF THE DRAWINGS

FIG. 4 is similar to FIG. 1 but illustrates another embodiment of the arrangement.

FIG. 5 is an elevational front view of a stimulus system constituting part of the arrangement of, and shown in a side view in, FIG. 3.

DESCRIPTION OF THE PREFERRED EMBODIMENTS

Figure 1:
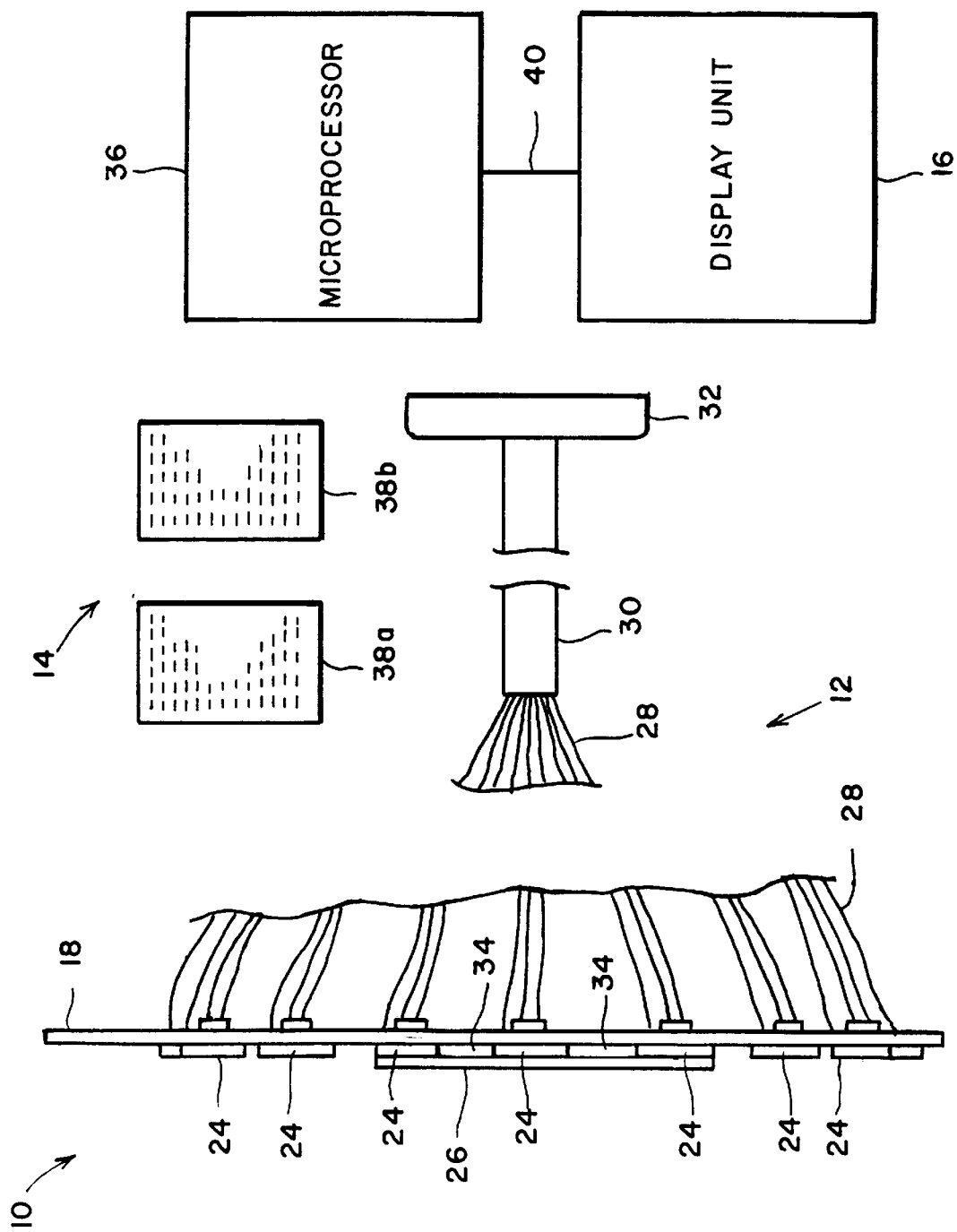
FIG. 1 is a schematic fragmentary illustration of an arrangement according to the invention for enhancing vision and/or hand-eye coordination.

Referring to FIG. 1, an arrangement according to the invention for enhancing vision and/or hand-eye coordination is identified by the numeral 10. The enhancing arrangement 10 includes a stimulus system 12, a control system 14 and a display unit 16.

Figure 2:
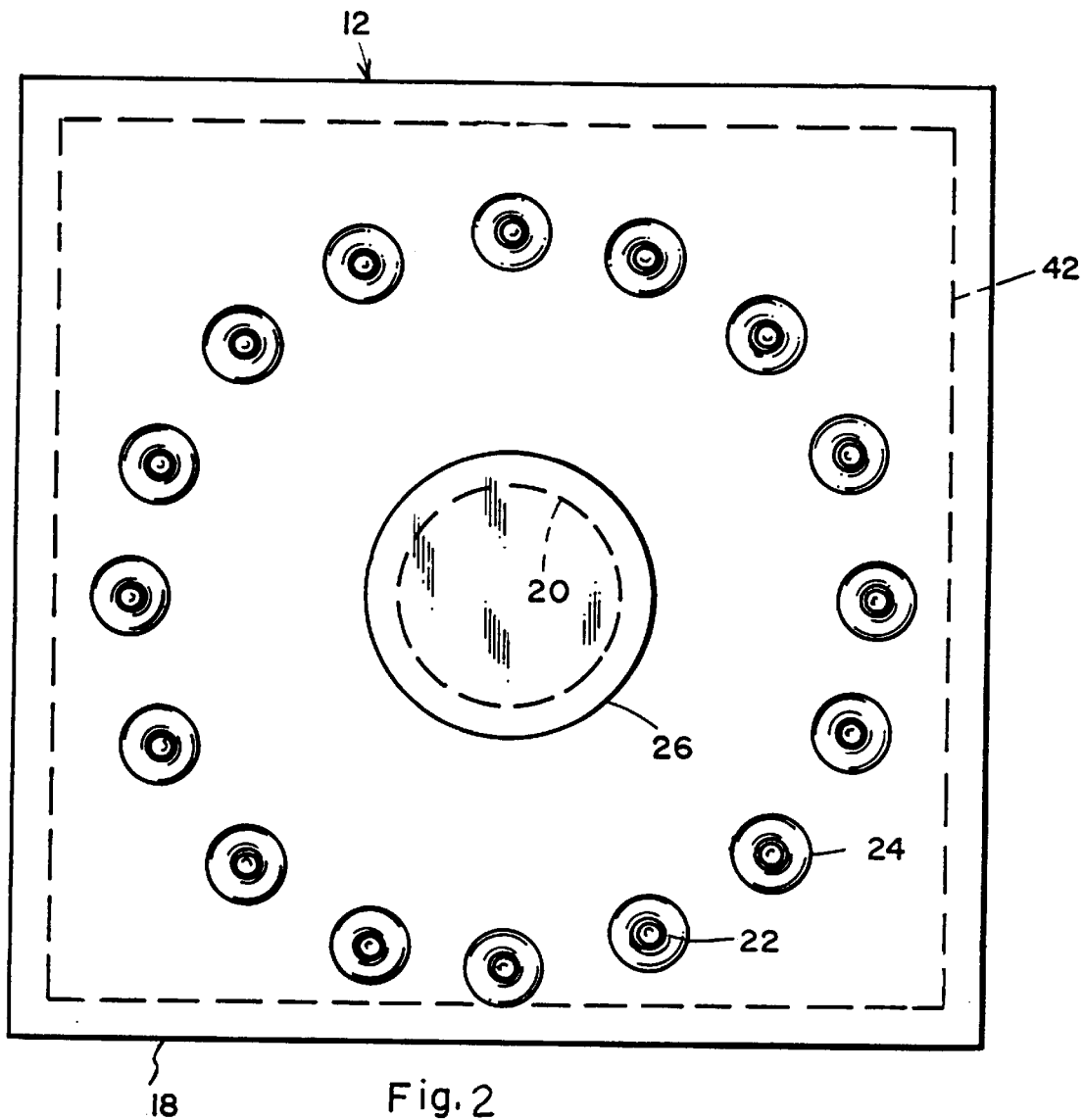
FIG. 2 is an elevational front view of a stimulus system constituting part of the arrangement of, and shown in a side view in, FIG. 1.

Considering FIG. 2 in conjunction with FIG. 1, the stimulus system 12 comprises a flexible carrier or support 18 in the form of a sheet or curtain. The sheet 18, which can be square or rectangular, is capable of being folded or rolled up. The sheet 18 is opaque and is provided with a central circular opening or transparent portion 20 which is surrounded by an annulus of stimulus lights or lamps 22. The stimulus lights 22 are preferably constituted by light-emitting diodes (LEDs). An annular touch pad or extinguishing element 24 circumscribes each of the LEDs 22. A color filter or colored filtering element 26 overlies the central opening 20. The color filter 26 can, for example, be formed from a thin sheet of colored plastic.

The LED annulus and central opening 20 are concentric. The relative position of the central opening 20 and the LED annulus is such that the LEDs 22 are in the peripheral vision range of a subject facing the sheet 18 from a distance much less than infinity with her/his head in line with, and her/his eyes approximately level with the center of, the opening 20.

Leads or conductors 28 extend from the LEDs 22 and the touch pads 24 to a tubular sheath 30. The sheath 30 has an open end through which the leads 28 enter the sheath 30, and a plug 32 is mounted at the opposite end of the sheath 30. The sheath 30 encases the portions of the leads 28 remote from the LEDs 22 and touch pads 24 to form a cable. The plug 32 is provided with a non-illustrated set of pins, and the leads 28 are connected to respective ones of the pins.

The LEDs 22 and the color filter 26 may be releasably connected to the sheet 18 by fasteners or fastening elements 34 such as hook-and-loop fasteners or snaps. It is also possible for the LEDs 22 and the color filter 26 to be permanently attached to the sheet 18. The touch pads 24 can be bonded or otherwise secured to the sheet 18, and each LED 22 is fixed relative to the sheet 18 and the adjacent touch pad 24 when the LED 22 is properly mounted on the sheet 18.

The control system 14 comprises a microprocessor 36 having an electrical receptacle for the plug 32. The control system 14 further comprises computer cards 38a and 38b which are insertable in the microprocessor 36 and carry different programs for operation of the LEDs 22. For instance, the computer card 38a may contain instructions for sequential illumination and extinguishment of the LEDs 22 circumferentially of the LED annulus while the computer card 38b may contain instructions for random illumination of the LEDs 22.

The microprocessor 36 is connected or connectible to the display unit 16 as indicated at 40. The display unit 16 can, for example, be constituted by a monitor or an oscilloscope.

The enhancing arrangement 10 can be used for different types of exercise or training, and two types of exercise will be described below.

To exercise the ability of the eyes to follow a moving object while keeping the head stationary, the sheet 18 with the LEDs 22 is hung on a wall or otherwise suspended. By way of example, this can be accomplished using suction cups. The plug 32 is inserted in the electrical receptacle of, and the computer card 38a is introduced into, the microprocessor 36. It is assumed that the computer card 38a is programmed to illuminate the LEDs 22 sequentially in circumferential direction of the LED annulus.

A subject stands or sits in front of, and at a specified distance from, the sheet 18. The subject faces the sheet 18 from a distance much less than infinity with her/his head in line with, and her/his eyes approximately level with the center of, the opening 20. When the subject is positioned in this manner, the LED annulus is in the peripheral vision range of the subject. Since the LEDs 22 are illuminated and extinguished sequentially in circumferential direction of the LED annulus, the effect is that of an object moving circumferentially of the annulus. The subject attempts to follow the simulated motion of the LEDs 22 with her/his eyes while keeping her/his head still.

By employing one or more computer cards in addition to the computer card 38a, it is possible to vary parameters such as the sequencing rate and the brightness of the LEDs 22. Changes in the brightness of the LEDs 22 allow the stimulus intensity to be varied.

Once the subject can comfortably follow the simulated motion of the LEDs 22 from the original distance, the subject can move closer to the sheet 18 and repeat the exercise.

In order to exercise hand-eye coordination, the sheet 18 with the LEDs 22 is hung over a window 42 shown in FIG. 2. The computer card 38b, which is assumed to be programmed for random illumination of the LEDs 22, is inserted in the microprocessor 36.

A subject positions herself/himself in front of the sheet 18 as before and focuses on a distant tree or other distant object through the color filter 26 and the opening 20. The subject is then fixated at virtual infinity which places the subject in a relaxed condition so that the subject can best benefit from the exercise. With the subject fixated at virtual infinity, the LEDs 22 are illuminated at random. When an LED 22 illuminates, the subject reaches out without moving her/his head or eyes and touches the touch pad 24 surrounding the illuminated LED 22. Upon touching the touch pad 24, the illuminated LED 22 is extinguished and another LED 22 illuminates. The programming can be such that an illuminated LED 22 extinguishes automatically if the associated touch pad 24 is not touched within a predetermined time interval.

The microprocessor 36 clocks the elapsed time between illumination of an LED 22 and touching of the associated touch pad 24. This data, together with the number of LEDs 22 which extinguished automatically, can be used to calculate a score or rating for the subject. The results can be displayed on the display unit 16.

Once a subject has finished exercising, the sheet 18 can be folded or rolled up. This can be accomplished with the LEDs 22 attached to the sheet 18 or disconnected therefrom. Folding or rolling up of the sheet 18 with the LEDs 22 attached causes the LEDs 22 to be gathered into a folded packet or a roll. On the other hand, if the LEDs 22 are disconnected before the sheet 18 is folded or rolled up, the LEDs 22 can be gathered to form a bundle.

Folding or rolling up of the sheet 18, and gathering of the LEDs 22, facilitates transport and storage of the sheet 18 and the LEDs 22. The entire enhancing arrangement 10 is preferably portable so that it can be readily taken to a location where it is needed.

The microprocessor 36 and the preprogrammed computer cards 38a, 38b allow the enhancing arrangement 10 to be economical and simple enough for home use.

The enhancing arrangement 10 lends itself to unique variations in exercise regimes. Thus, the rod cells and cone cells responsible for sight have different spectral sensitivities and are not uniformly distributed over the retina. If a subject is placed in a darkened room, the sensitivity of the rod cells increases over time by as much as six orders of magnitude after about 45 minutes. On the other hand, the sensitivity of the cone cells does not increase significantly so that the sensitivity ratio of rod cells to cone cells increases substantially. Inasmuch as the area of the retina responsible for central vision is populated exclusively by cone cells while the area responsible for peripheral vision is populated almost entirely by rod cells, the effective visual field of the subject changes from that in daylight.

The sensitivity increase of the rod cells is not affected by red light having a wavelength greater than about 640 nm. Accordingly, if the color filter 26 were red and the LEDs 22 green, a subject in a darkened room with the sheet 18 hung over one of the windows would have an increased awareness of the LEDs 22 in her/his peripheral vision range.

Conversely, peripheral awareness could be reduced by making the color filter 26 blue and the LEDs 22 red.

The LEDs 22 can be of the type which are capable of emitting red light as well as green light. This makes it possible to employ the LEDs 22 with both a red color filter and a blue color filter.

Figure 3:
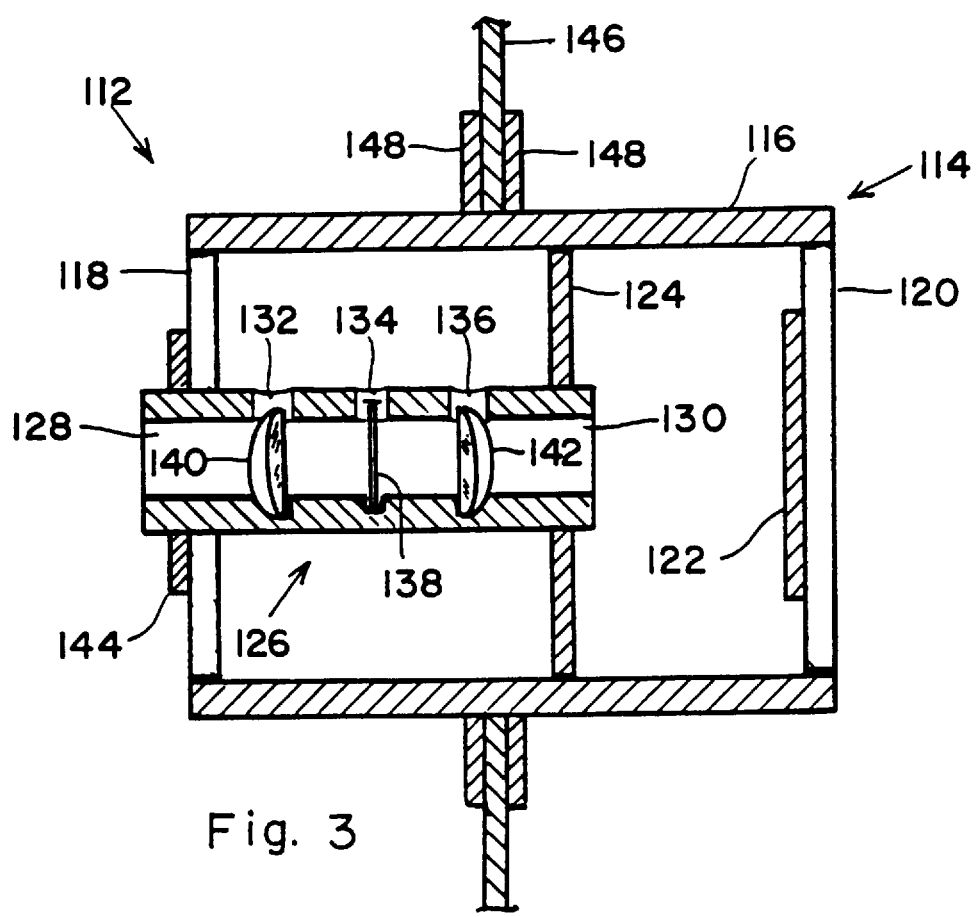
FIG. 3 is a fragmentary sectional view of an additional embodiment of an arrangement in accordance with the invention for enhancing vision and/or hand-eye coordination.

FIG. 3 shows a stimulus system 112 which achieves fixation at optical infinity.

The stimulus system 112 includes a cylindrical housing 114 having a cylindrical peripheral wall 116 and end walls 118 and 120. An object 122, which is preferably black-and-white, is centrally mounted on the inner surface of the end wall 120. The object 122 can, for instance, be a black-and-white photograph. The object 122 is illuminated by an annular light source 124 in the interior of the housing 114. The light source 124 has a central opening in line with the object 122 and with a central opening in the end wall 118.

The stimulus system 112 further includes a tubular lens holder 126 having opposite open ends 128 and 130. The lens holder 126, which may be cylindrical, is provided with three slots 132, 134 and 136 between the open ends 128,130. The middle slot 134 accommodates a removable color filter or colored filtering element 138 while the two remaining slots 132 and 136 accommodate removable concavo-convex lenses 140 and 142. The lenses 140,142 are positioned back-to-back, that is, with the concave sides of the lenses 140,142 facing one another.

The lens holder 126 can be removably mounted in the housing 114. To this end, the lens holder 126 is dimensioned to be received in the central openings of the housing end wall 118 and light source 124 with a light friction fit. The lens holder 126 is inserted in the housing 114 by passing the open end 130 through the central opening of the housing end wall 118 and into the central opening of the light source 124. A collar 144 is provided at the open end 128 of the holder 126 and constitutes a stop or abutment. When the collar 144 abuts the housing end wall 118, the lens holder 126 is properly positioned in the housing 114. In this position, the object 122 is at the focal distance from the convex surface of the lens 142 and, to a subject, the image of the object 122 is at optical infinity.

The stimulus system 112 additionally includes a flexible carrier or support 146 in the form of a sheet. The sheet 146 can be identical to the sheet 18 of FIGS. 1 and 2 and is provided with a like array of touch pads and stimulus lights. The housing 114 fits in the central opening of the sheet 146 and is releasably connectible to the latter by fasteners or fastening elements 148 such as hook-and-loop fasteners or snaps.

One or both of the end walls 118,120 of the housing 114 may be removable. The housing 114 need not be cylindrical and can, for example, be square or rectangular. In such a case, the central opening in the sheet 146 will be square or rectangular.

With reference to FIGS. 4 and 5, the same numerals as in FIGS. 1 and 2 plus two hundred identify corresponding elements.

The enhancing arrangement 210 differs from the enhancing arrangement 10 in that the sheet 218 is not provided with a central opening. Furthermore, a small microphone 242 is mounted at the top center of the sheet 218 while two small microphones 244a and 244b are respectively mounted near the bottom corners of the sheet 218. Leads or conductors 246 extend from the microphones 242,244a,244b to the sheath 230. The microphones 242,244a,244b may be releasably connected to the sheet 218 by fasteners or fastening elements 248 such as hook-and-loop fasteners or snaps.

Non-illustrated audio amplifiers are associated with the microphones 242,244a,244b. These amplifiers have a bandpass filter characteristic which is selected so that the microphones 242,244a,244b respond to impacts on the sheet 218 but not to ambient sounds or voices.

In operation, the sheet 218 with the stimulus lights 222 and the microphones 242,244a,244b is freely suspended. A subject stands in front of the sheet 218 at some distance from the latter. One of the stimulus lights 222 is illuminated and, together with the associated touch pad 224, forms a target which the subject attempts to hit with a ball or some other object.

The sound of the impact is recorded by the microphones 242,244a,244b which generate audio signals. The signals are digitized and sent to the microprocessor 236 which determines the location of the impact, the strength of the impact and the elapsed time between stimulus light illumination and impact. The results can be shown on the display unit 216 and may be used to calculate a score or rating calculate a score or rating for the subject.

It is possible to mount the microphones 242,244a,244b on the sheet 18 of FIGS. 1 and 2. In such an event, it may be desirable to have a protective sheet which can be placed over the color filter 26 or the central opening 20 of the sheet 18. The protective sheet may be releasably connectible to the sheet 18.

The stimulus system 12 of FIGS. 1 and 2, and the stimulus system 112 of FIG. 3, allow a subject to fixate at virtual infinity and optical infinity, respectively. This results in a relaxed atmosphere which enables the subject to obtain maximum benefit from the exercise being performed.

The foldable or bendable character of the sheet 18,146, 218 makes it possible to transport the stimulus system 12,112,212 with relative ease. The system 12,112,212 is then not restricted to use at a single location. Use of the system 12,112,212 at different locations may be facilitated by employing a portable microprocessor 36,236 and a portable display unit 16,216.

The touch pads 24,224 permit a pulse to be generated with light pressure. By designing the touch pads 24,224 to circumscribe the LEDs 22,222, good targets are obtained.

The microphones 242,244a,244b make it possible not only to measure the timing and strength of impacts but also to determine accuracy.

The use of a microprocessor 36,236 which accepts computer cards 38a,38b,238a,238b allows a subject to have a variety of training and exercise regimes at her/his disposal. Furthermore, the change from one training or exercise regime to another can be carried out simply and rapidly.

The releasable mounting of the LEDs 22,222 on the sheet 18,218 results in great flexibility. Thus, it permits one or more of the LEDs 22,222 to be removed in order to obtain different LED patterns on the sheet 18,218.

Likewise, the releasable mounting of both the LEDs 22 and the color filter 26 on the sheet 18 enables different combinations of LEDs 22 and color filters 26 to be set up quickly and easily.

Various modifications are possible within the meaning and range of equivalence of the appended claims.

I claim:

1. An arrangement for enhancing the vision or hand-eye coordination of a subject comprising:
    a plurality of light sources;
    a control system for said light sources; and
    means for permitting the subject to fixate at virtual or optical infinity while maintaining said light sources within view of the subject.

2. The arrangement of claim 1, wherein said permitting means comprises a carrier for said light sources, said carrier having a substantially transparent portion, and said carrier being designed to support said transparent portion and said light sources within view of the subject.

3. The arrangement of claim 2, wherein said carrier is substantially opaque except for said transparent portion.

4. The arrangement of claim 2, further comprising a substantially transparent filter for covering said transparent portion.

5. The arrangement of claim 4, wherein said filter is red and said light sources emit green light, or said filter is blue and said light sources emit red light.

6. The arrangement of claim 2, wherein said carrier is foldable or roll-up.

7. The arrangement of claim 2, further comprising at least one audio element for sensing impacts upon said carrier.

8. The arrangement of claim 1, further comprising an extinguishing element for at least one of said light sources, said extinguishing element being designed to at least partially circumscribe said one light source and to extinguish said one light source in response to touch.

9. The arrangement of claim 8, wherein said extinguishing element is circumferentially complete and defines an opening for said one light source.

10. The arrangement of claim 8, wherein said control means comprises means for sensing, and for recording data relating to, extinguishing of said one light source by said extinguishing means.

11. The arrangement of claim 1, wherein said permitting means comprises lens means, and an object spaced from said lens means by a distance which substantially equals a focal length of said lens means.

12. The arrangement of claim 11, wherein said lens means comprises a pair of lenses having concave sides which face one another.

13. The arrangement of claim 11, wherein said lens means comprises a pair of spaced lenses; and further comprising a filter insertable between said lenses.

14. The arrangement of claim 13, wherein said filter is red and said light sources emit green light, or said filter is blue and said light sources emit red light.

15. The arrangement of claim 11, wherein said permitting means further comprises a holder for said lens means, a housing for receiving said holder, and an illumination source, said object being mounted in said housing, and said illumination source being arranged to illuminate said object.

16. The arrangement of claim 15, wherein said permitting means is portable.

17. The arrangement of claim 1, wherein said control system comprises a computer, and interchangeable software for said computer programmed to control said light sources.

18. An arrangement for enhancing vision or hand-eye coordination comprising:

a plurality of light sources;

a control system for said light sources; and a foldable or roll-up carrier for said light sources.

19. An arrangement for enhancing vision or hand-eye coordination comprising:

a plurality of light sources;

an audio element;

a carrier for said light sources and said audio element; and a control system for said light sources and for recording data generated by said audio element in response to impacts on said carrier.

20. An arrangement for enhancing vision or hand-eye coordination comprising:

a plurality of light sources;

a control system for said light sources; and an extinguishing element for at least one of said light sources, said extinguishing element being designed to at least partially circumscribe said one light source and to extinguish said one light source in response to touch.

21. The arrangement of claim 20, wherein said extinguishing element is circumferentially complete and defines an opening for said one light source.

22. A method of enhancing the vision or hand-eye coordination of a subject comprising the steps of:

fixating at virtual or optical infinity, the fixating step being performed by the subject;

illuminating light sources within view of the subject during the fixating step; and reacting to illumination of said light sources, the reacting step being performed by the subject.

23. The method of claim 22, wherein said light sources are illuminated sequentially.

24. The method of claim 22, wherein the reacting step comprises reaching for a light source upon illumination of the same.

25. The method of claim 22, wherein the illuminating and reacting steps are performed in a darkened atmosphere and the fixating step comprises observing an illuminated object; and further comprising the step of filtering illumination from said object.

26. The method of claim 25, wherein said light sources emit green light and the filtering step comprises coloring illumination from said object red.

27. The method of claim 25, wherein said light sources emit red light and the filtering step comprises coloring illumination from said object blue.

28. The method of claim 22, wherein the reacting step comprises extinguishing an illuminated light source by touch.

29. A method of enhancing the vision or hand-eye coordination of a subject comprising the steps of:

distributing light sources within view of the subject;

illuminating said light sources;

reacting to illumination of said light sources, the reacting step being performed by the subject; and gathering said light sources subsequent to the illuminating and reacting steps.

30. The method of claim 29, wherein said light sources are mounted on a carrier and the gathering step comprises folding or rolling up said carrier.

31. A method of enhancing the vision or hand-eye coordination of a subject comprising the steps of:

providing light sources;

illuminating one of said light sources within view of the subject;

reacting to illumination of said one light source by impacting an area around said one light source, the reacting step being performed by the subject; and recording the sound of the impact.

32. A method of enhancing the vision or hand-eye coordination of a subject comprising the steps of:

providing light sources;

illuminating one of said light sources within view of the subject; and reacting to illumination of said one light source, the reacting step being performed by the subject and including extinguishing said one light source by touch.

* * * * *